United States Patent [19]

Grote et al.

[11] Patent Number: 4,827,845

[45] Date of Patent: May 9, 1989

[54] FORMATION OF HYDROXY ARYL CARBOXYLIC ACIDS AND ESTERS

[75] Inventors: Dace Grote, Columbus, Ohio; William L. Embry, Lilburn, Ga.; Kenneth W. Barnett, Worthington, Ohio

[73] Assignee: Ashland Oil, Inc., Columbus, Ohio

[21] Appl. No.: 102,016

[22] Filed: Sep. 23, 1987

[51] Int. Cl.$^4$ .............................................. C07C 51/10
[52] U.S. Cl. ...................................... 502/406; 560/56; 560/75; 549/299; 549/302
[58] Field of Search ......................................... 562/406

[56] References Cited

FOREIGN PATENT DOCUMENTS 2537204  3/1976  Fed. Rep. of Germany .
5027136  2/1980  Japan ................................... 562/406

OTHER PUBLICATIONS

M. A. Heitkamp: "Fungal Metabolism of Tert-Butylphenyl Diphenyl Phosphate", Applied and Environmental Microbiology, Aug. 1985, pp. 265–273.

R. D. Burpitt et al; "The Reactions of Dimethylketene With Alpha-Dicarbonyl and Related Compounds" J. Org. Chem., vol. 36, No. 16, 1971.

A. Jonsson; "Studies on Antimetabolites": Acta Chemica Scandinavica, 8 (1954), 1211–1217, vol. 7.

B. Carnmalm et al; "Potential X-ray Contrast Agents"; Acta Pharm. Succica 11, 175 184 (1974).

*Primary Examiner*—Paul J. Killos
*Attorney, Agent, or Firm*—Wood, Herron & Evans

[57] ABSTRACT

Hydroxy aryl carboxylic acids are formed by reacting a hydroxy aryl compound, such as phenol, with a ketone, such as acetone and carbon monoxide in the presence of a strong acid. The preferred embodiment is the one step formation of 2-methyl-2-(p-hydroxyphenyl) propionic acid from phenol, acetone and carbon monoxide in the presence of hydrofluoric acid. When this reaction is conducted in the presence of methanol the corresponding methyl ester is formed.

16 Claims, No Drawings

FORMATION OF HYDROXY ARYL CARBOXYLIC ACIDS AND ESTERS

FIELD OF THE INVENTION

The present invention relates to an alkylation/carbonylation reaction. More particularly, the present invention relates to the strong acid catalyzed alkylation of a phenol or phenol derivative by a ketone in the presence of carbon monoxide to produce an aromatic carboxylic acid. Optionally the reaction may be carried out in the presence of added methanol to produce the corresponding methyl ester.

Further, the present invention relates to a method of forming hydroxy aromatic acids and esters by reacting aromatic compounds such as phenol, resorcinol, ortho-cresol, dimethyl phenol, napthol and the like with ketones such as acetone or 2-butanone together with carbon monoxide catalyzed by a strong acid.

A preferred embodiment of the present invention relates to a method of forming 2-methyl-2-(p-hydroxyphenyl) propionic acid by reacting phenol with acetone and carbon monoxide in the presence of concentrated hydrofluoric acid.

BACKGROUND

The polymer and pharmaceutical industries frequently require difunctional acids or esters thereof. For example, difunctional monomers such as phenolic acids are used as capping agents or termonomers in polyester formation. One particular compound so utilized is p-hydroxyphenyl acetic acid. This is a particularly expensive monomer formed by a complex reaction sequence. Substituted phenol acids are also used in pharmaceuticals where benzopyran derivatives are anti-asthma drugs.

A particularly desirable product in this family of compounds is 2-methyl-2-(p-hydroxyphenyl) propionic acid, a homolog of p-hydroxyphenyl acetic acid. Synthetic routes leading to this compound involve several steps and in general, afford low to modest yields of the desired product. For example, Defensive Publication No. T908009 describes the production of this propionic acid by reacting p-quinone with dimethylketene and subsequent hydrogenation. This chemistry is extremely costly and, in fact, cost prohibitive. Other multi-step syntheses are also cost prohibitive and are described, for example, in German Offen. No. 2,537,204 (Aug. 23, 1974), Jonsson, N. A., e.t., *Acta Pharm. Suec* 164–167 (1974); Martin, J. C., et al. *J. Org. Chem.*, 36 (16) 2216–22 (1971) and Jonsson, A. *Acta Chem. Scand.* 8, 1211 (1954).

SUMMARY OF THE INVENTION

The present invention is premised on the realization that phenol or a phenol derivative having at least one reactive site ortho or para to the hydroxy group will react with a ketone and carbon monoxide in the presence of a strong acid to form a hydroxy aromatic carboxylic acid.

Further, the invention is premised on the realization that carrying out the above reaction in the presence of added methanol leads to formation of the methyl ester compounds. These are formed by reacting a hydroxy aromatic compound having a reactive site ortho or para to the hydroxy group with a ketone, carbon monoxide and methanol in the presence of a strong acid.

Further, the present invention is premised on the realization that both monocyclic and polycyclic aromatic compounds can function in the above reaction to form hydroxy aromatic acids and esters.

The present invention is further premised on the realization that aromatic ethers having a reactive site ortho or para to the ether group function to form a corresponding aromatic ether carboxylic acid when reacted with a ketone and carbon monoxide in the presence of a strong acid.

In particular, the present invention is premised on the realization that 2-methyl-2-(p-hydroxy phenyl) propionic acid can be formed by reacting phenol, acetone and carbon monoxide under pressure in the presence of a strong acid such as 90% hydrofluoric acid. Further advantages of the present invention will be appreciated in light of the following detailed description.

DETAILED DESCRIPTION

According to the present invention, phenol or a phenol derivative ($Ar-O-R_1$) reacts with a ketone and carbon monoxide in the presence of an acid to form an aromatic carboxylic acid wherein Ar represents a benzene ring. More particularly the aromatic compound should have the following general formula:

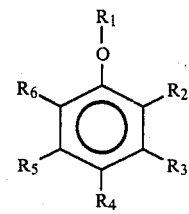

wherein $R_1$ represents either hydrogen, methyl, or aryl.

$R_2-R_6$ represents one or more of the following: hydrogen, $C_1-C_{18}$ alkyl, halogen, hydroxyl, $C_1-C_{18}$ alkyl halide, aryl alkyl.

Basically $R_2-R_6$ cannot be any group which would react with the strong acid, carbon monoxide or the reactants under the reaction conditions of the present invention.

Further, there must be a reactive site ortho or para to the $-O-R_1$, group. In other words, at least one of $R_2$, $R_4$ or $R_6$ must represent hydrogen.

Representative phenols and derivatives include phenol, ortho, para or meta $C_1-C_{12}$ alkyl phenol such as cresols, resorcinol, dimethyl phenol, dichloro phenol, Bisphenol A (4,4'-isopropylidene diphenol) and its derivatives.

Suitable ethers are anisole and diphenyl ether, (i.e., wherein $R_1$ is methyl or phenyl).

The phenol or derivative may be a polycyclic aromatic compound wherein there is a reactive site one or three carbon atoms from a hydroxy or ether group. Where the aromatic compound is a naphthalene derivative it can be represented by the following general formula:

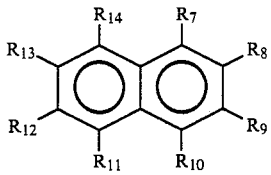

wherein at least one of $R_7$-$R_{14}$ represents —O—$R_1$ and there is at least one reactive site within one or three carbon atoms of —O—$R_1$. The remainder of $R_7$-$R_{14}$ represent hydrogen, $C_1$-$C_{18}$ alkyl, halogen, hydroxyl, $C_1$-$C_{18}$ alkyl halide, $C_1$-$C_{18}$ alkyl ether, aryl alkyl and the like. These are the same groups represented by $R_2$-$R_6$.

Generally there is no limitation on the particular ketone suitable for use in the present invention. Generally, the ketone will be a $C_3$-$C_{20}$ ketone. Suitable ketones include acetone, butanone, pentanone, and aromatic ketones such as methyl phenyl ketone and diphenyl ketone. The preferred ketone is acetone.

The alkylation/carbonylation reaction of the present invention is conducted in the presence of a strong acid. Suitable strong acids include hydrofluoric acid, sulfuric acid, and hydrochloric acid. For the present invention strong acid also includes anhydrous HF and HCl. The preferred acid in the present invention is 80–90% aqueous hydrofluoric acid to maximize yield. Anhydrous hydrofluoric acid may be preferred to minimize corrosion.

Reaction

The alkylation/carbonylation reaction is conducted in a pressurized reaction vessel. Continuous, batch and semi-batch reactors constructed of inert materials such as Hastelloy C brand alloy can be used in the present invention. The reaction can be conducted under various conditions. Yield controlling parameters include molar ratio of reactants, water content, feed time, pressure, temperature and reaction time.

As an example of semi-batch operation, the reactor is charged with the strong acid catalyst, and pressurized with carbon monoxide and heated. The ketone and phenol or derivative are combined to form a fluid mixture which is then pumped into the reaction vessel. Feed time refers to the time the feed mixture is being added to the acid in the presence of CO. Carbon monoxide pressures are maintained at the desired level for the desired reaction time. Optionally, the phenol or derivative may be added to the reactor before or at the same time as the strong acid catalyst. The ketone then would be charged to the reaction mixture. It will be understood by one of skill in the art that the addition rate, $H_2O$ content, time of addition, temperature, pressure, molar ratios are interrelated and can be modified further to provide differing results.

If the methyl ester of the acid is desired, the reaction remains the same with methanol charged as a reactant.

In the present batch reactor configuration, it is preferable to have a molar excess of ketone. Generally, it has been found that a molar ratio in the range of 1.1:1 up to 5:1 of ketone to phenol or phenol derivative provides higher product selectivity. Preferably the molar ratio should be about 3:1 ketone to phenol or phenol derivatives. Generally excess acid (20 moles HF:1 mole of phenol or derivative) is employed.

Water is not necessary to conduct the present reaction. However, it was found that the use of anhydrous acid, such as hydrogen fluoride, reduced selectivity to the aromatic acid. Accordingly, it is preferable to use a catalyst which includes a strong acid mixed with approximately 10–20% water. Additional water is undesirable due to its corrosive effect when combined with the acid.

Preferably, the reaction is conducted within 1–300 minutes (5 hours). At longer reaction times, the conversion of the phenol is increased but the selectivity to the aromatic acid decreases. Accordingly, it is preferred to maintain the reaction time around 120–130 minutes.

Temperature is an important factor in increasing yields and selectivities. Maximum selectivity and yield is obtained at about 75° C. At 20° C. or less, no reaction occurs. At temperatures in excess of 75° C. conversion of the aromatic alcohol or ether compound increases but selectivity towards the acid decreases. Accordingly, reaction temperatures should be greater than 20° C. and less than 90° C. and preferably about 75° C.

The reaction pressure is controlled by addition of carbon monoxide to the closed reaction vessel. Increasing pressure therefore increases available carbon monoxide. The reaction will occur at ambient pressure if carbon monoxide is available as well as pressures in excess of 3000 psi and higher. Maximum selectivity for the aromatic alcohol or ether is obtained when the pressure is maintained between 400–3000 and most preferably at about 1600 to 2300 psig.

In addition to the desired hydroxy aryl carboxylic acid, a number of co-products are also formed. For example, when phenol is reacted with acetone and carbon monoxide in the presence of hydrogen fluoride, 2-methyl-2-(p-hydroxyphenyl) propionic acid is obtained as well as 3,3,Dimethyl 2(3H)-benzofuranone, and Bisphenol-A.

The present invention will be further appreciated in light of the following detailed examples. The Roman numerals refer to the Structure Guide.

Example 1: Formation of 2-Methyl-2-(p-hydroxyphenyl) Propionic Acid (I)

Anhydrous hydrogen fluoride (AHF) (90 grams-4.5 moles) is added to a sealed 300 cc Hastelloy C Autoclave Engineers Magnedrive brand reactor containing 10 grams (0.55 moles) of water. The stirred reactor is pressurized with CO to a total pressure of 1611 psig (111 bars) at 71° C. Over a period of 57 minutes a solution of 43.7 grams of acetone (0.75 moles) and 23.6 grams phenol (0.25 moles) is pumped with a reciprocating piston pump to the vapor space of the reactor. The reactor contents are stirred for an additional 236 minutes at temperatures between 71° and 74° C. The pressure range of 1917–2305 psig is maintained with CO repressurization as CO is consumed. The reactor is cooled, vented and emptied over wet ice to provide an aqueous HF concentration of about 15%. Analysis is run on toluene and methyl isobutyl ketone (MIBK) extracts.

Using GC internal standard techniques of silylated reaction products, the toluene extracts (four extractions, total 1200 ml) contain the o-substituted and dehydrated lactone (VIII), unreacted phenol, Bisphenol-A (IX), by-products as self-esters of (I), and ketones and some 2-methyl-2-(p-hydroxyphenyl) propionic acid (I). $Na_2SO_4$ (400 gms) is added to the aqueous phase followed by extraction with four volumes of MIBK. The total MIBK solubles (100–1300 ml) are treated with glass wool and $Na_2SO_4$ to neutralize residual HF and analyzed by GC techniques. The non-volatiles from the MIBK extraction were 90% pure hydroxy aryl acid (I) after solvent removal. Overall, 81% conversion of phenol was realized yielding 20.9 grams (I) (57% selectivity based on phenol), 2.7 gms lactone (VIII) (9% selectivity) and 0.5 gms Bisphenol-A (IX) (2% selectivity). The overall yield of the desired title compound (I) was 48%.

Example 2

The procedure and analysis are followed as in Example 1 studying the effect of $H_2O$ concentration in HF. At 70°–77° C., 1400–2400 psig, addition rates maintained at 0.09–0.12 moles phenol/mole HF $hr^{-1}$. The results are shown in the table.

| % HF/$H_2O$ | Molar Ratios HF/Phenol/ Acetone/$H_2O$ | Total Reaction Time (min) | % Conv | % Selectivities I | VIII | IX |
|---|---|---|---|---|---|---|
| 100 | 18/1/3/0 | 270 | 88 | 16 | 17 | 12 |
| 99 | 10/1/1.2/0.1 | 130 | 74 | 33 | 12 | 7 |
| 95 | 10/1/1.2/0.6 | 206 | 75 | 30 | 16 | 4 |
| 90 | 10/1/1.2/1.2 | 210 | 63 | 51 | 9 | 9 |
| 80 | 10/1/1.2/2.8 | 183 | 51 | 60 | 4 | 9 |
| 48 | 8/1/3/9 | 180 | 8 | 0 | 0 | 82 |

Example 3

The procedure, charges, and analysis are followed as in Example 1, varying the reaction temperature. The addition rate of the phenol and acetone reactants are maintained at 0.06 moles phenol/mole HF $hr^{-1}$, pressure range of 1500–2400, and reaction time of 210–293 minutes. The results are:

| Temp | % Phenol Conv | % Selectivities I | VIII | IX |
|---|---|---|---|---|
| 59–62° C. | 57 | 51 | 5 | 8 |
| 71–75 | 86 | 56 | 7 | 2 |
| 87–93 | 93 | 26 | 15 | 0 |

Example 4

The procedure, analysis and charges are followed as in Example 1, varying pressure and slower phenol and acetone reactants' addition rate at lower pressures. After 273–293 minutes:

| Pressure | Addition Rate | % Phenol Conv. | % Selectivities to I | VIII | IX |
|---|---|---|---|---|---|
| 1610–2305 | 0.06 | 81 | 57 | 8 | 2 |
| 406–482 | 0.07 | 80 | 31 | 7 | 3 |
| 470–502 | 0.01 | 59 | 32 | 12 | 7 |

Example 5

The procedure and charges are followed as in Example 1. The results compare residence time and reactant feed time at 1400–2300 psig:

| Time of Addition (min) | Total Reaction Time (min) | % Phenol Conv. | % Selectivities to I | VIII | IX |
|---|---|---|---|---|---|
| 9 | 9 | 7 | 31 | 4 | 38 |
| 62 | 62 | 34 | 49 | 9 | 12 |
| 57 | 293 | 81 | 57 | 8 | 2 |
| 134 | 134 | 50 | 42 | 10 | 0 |

Example 6

Following procedures and conditions as in Example 1, maintaining a 90% HF/$H_2O$ carbonylation medium and 72°–78° C., the effect of dilution by the acid medium is revealed by the following results at 240–283 minute reaction times. Phenol/acetone reactant feed rates of 0.05–0.08 phenol/HF molar $hr^{-1}$ are maintained, as are pressures of 1200–2100 psig:

| Molar Ratios HF/Phenol/Acetone/$H_2O$ | % Phenol Conv | % Selectivities to I | VIII | IX |
|---|---|---|---|---|
| 7.5/1/3/0.9 | 54 | 18 | 5 | 19 |
| 10/1/3/1.2 | 65 | 34 | 8 | 8 |
| 13.8/1/3/1.7 | 84 | 51 | 8 | 2 |
| 18/1/3/2.2 | 76 | 57 | 9 | 3 |
| 30/1/3/3.7 | 84 | 45 | 13 | 3 |

Example 7

Following procedures and conditions reported in Example 1, the level of phenol and acetone is varied with 90% HF/$H_2O$ reaction medium maintaining an 18/1.0 molar charge ratio of HF to the limiting reactant (phenol or acetone). At 1200–2000 psig and 273–279 minutes, total reaction times, the following results are obtained:

| Molar Ratios Phenol/Acetone | % Phenol Conv | % Selectivities to (I) | (VIII) | (IX) |
|---|---|---|---|---|
| 3/1 | 35 | 30 | 15 | 17 |
| 1/1.2 | 67 | 33 | 21 | — |
| 1/2 | 76 | 52 | 12 | 5 |
| 1/3 | 76 | 57 | 9 | 3 |
| 1/6 | 63 | 18 | 12 | 0 |

Example 8

The following illustrates the pumping of the acetone and phenol mixture above and below the liquid surface of the 90% HF/$H_2O$ medium is not a factor in altering selectivities to the phenol acid. Following procedures and charges as cited in Example 1, at 57°–62° C., 1500–2200 psig and total reaction times of 210 and 128 min, respectively, the following results are obtained:

| Mode of Addition | % Phenol Conv. | % Selectivities to (I) | (VIII) | (IX) |
|---|---|---|---|---|
| To Vapor Space | 57 | 51 | 5 | 8 |
| Below Liquid | 42 | 53 | 4 | 16 |

Example 9

The procedures and charges of Example 1 are followed except acetone is charged to the 90% HF/$H_2O$ reaction medium containing phenol. After a total reaction time of 212 minutes, an 84% phenol conversion yielded 52% selectivity to the title compound (I), 10% selectivity to lactone (VIII) and 2% selectivity to Bisphenol-A (IX) based on phenol. A total 44% yield (19.8 g) of the phenol acid (I) was obtained.

Example 10: Methyl, 2-Methyl 2-(p-Hydroxyphenyl) Propionate (IA)

A solution of 18.5 g phenol (0.20 moles) and 34.2 g acetone (0.59 moles) is pumped into a CO pressurized reactor containing 74 g AHF (3.7 moles), 24.6 g methanol (0.77 moles) and 50 g cyclohexane. At 1200 psig total pressure and 75° C., the acetone/phenol mixture is pumped into the vapor space (53 minutes total time) and the reactor pressure is maintained with CO at 1700–1930 psig. After a total reaction time of 273 minutes (inclusive of phenol/acetone addition), 8.6 g of methyl ester (IA) is recovered as cyclohexane and methyl isobutyl ketone soluble from aqueous HF. With an 80% phenol conversion, this represents a 28% selectivity and 22% yield of the ester (IA) (m.p.=107–111° C.) based on phenol.

Example 11: Methyl, 2-Methyl 2-(p-Hydroxyphenyl) Propionate (IA)

A solution of 18.5 g phenol (0.20 moles) and 34 g acetone (0.59 moles) is pumped into a CO pressurized, stirred reactor containing 24.6 g methanol (0.77 moles) 90 g AHF (4.5 moles), and 10 g water (0.56 moles). At 1260 psi, the phenol acetone mixture is pumped at 72°–75° C. in 60 minutes to a total pressure of 1645 psi. After a total reaction time of 273 minutes and maintaining a pressure range of 1640–1940 psi, the reactor contents are cooled, vented and collected over wet ice. Extraction with cyclohexane and MIBK yields a total of 9.31 g as (IA), representing a 33% selectivity based on phenol with a 74% phenol conversion.

Example 12: 2-Methyl 2-(p-Hydroxyphenyl) Butanoic Acid (II)

A solution of 23.1 g phenol (0.25 moles) and 53.1 g 2-butanone (0.74 moles) is pumped into a CO pressurized reactor containing 10 g water (0.56 moles) and 91 g AHF (4.55 moles). At a starting pressure of 1430 psig and 74°–81° C., the phenol and 2-butanone are charged in (66 minutes pumping time). After complete addition of the reactants, the pressure decreases from 2015 psig to 1700 psig over an additional 188 minutes at the reaction temperature. 8.4 g of (II) is isolated as toluene and methyl isobutyl ketone soluble from an aqueous HF extraction representing 55% phenol conversion and 32% selectivity to (II). Crystallization from toluene and CHCl$_3$ yielded the product (m.p. 129°–131° C.) with structure II verified by nmr.

Example 13: Mono$^{(III)}$ and Di-Lactone$^{(IV)}$ Product from Resorcinol and Acetone A solution of 22 g of resorcinol (0.2 moles) and 35 g acetone (0.60 moles) is pumped into a CO pressurized reactor containing 10 g H$_2$O (0.55 moles) and 90 g HF (4.5 moles). At a starting pressure of 1480 psig and 74°–77° C., the resorcinol and acetone are charged in 44 minutes maintaining CO pressures of 1530–1940 psig. After a total reaction time of 285 minutes, a 99% resorcinol conversion is attained. 9.9 g of the di-lactone product (IV) (m.p.=238° C.) is obtained along with 23 grams of the monolactone (III) (GC/mass spectroscopic identification).

Example 14: 2-Methyl-2-(3-Methyl-4-Hydroxyphenyl) Propionic Acid (V)

A solution of 27.0 g o-cresol (0.25 moles) and 43.7 g acetone (0.75 moles) is pumped into a CO pressurized, stirred reactor containing 10 g water (0.56 moles) and 91 g hydrogen fluoride (4.55 moles). At a starting pressure of 1464 psi and 71°–74° C., the reactants are charged within 56 minutes to a final pressure of 1980 psi. After a total reaction time of 302 minutes (inclusive of reactant feed time), while maintaining a pressure range of 1645–1917 psi, the reactor contents are cooled, collected over ice and extracted with toluene and MIBK. The three isomers represented 16.1 g or 34% selectivity to acids with a 97% o-cresol conversion. The title compound (V) is crystallized from triclene yielding the major isomer (60% of total), nmr pure, with m.p.=145°–146° C.

Example 15: 2-Methyl 2-(4-Hydroxyphenyl) Propionic Acid (I)

A solution of 28.5 g Bisphenol-A (IX) (0.12 moles) and 36.4 g acetone (0.63 moles) is pumped into a CO pressurized reactor containing 92 g HF (4.6 moles) and 10 g H$_2$O (0.56 moles). At a starting pressure of 1530 psig and 72°–75° C., the (IX) and acetone reactants are pumped in 64 minutes to a final pressure of 1760 psig. After a total reaction time of 293 minutes, maintaining pressures of 1930–2210 psig, a 98% (IX) conversion yields 20.3 g or 44% selectivity to (I).

Example 16: 2-Methyl 2-(3,5 Dimethyl 4-Hydroxyphenyl) Propionic Acid (VI)

A solution of 30.7 g of 2, 6 dimethylphenol (0.25 moles) and 43.7 g acetone (0.75 moles) is pumped into a CO pressurized reactor containing 10 g H$_2$O and 92 g HF (4.6 moles). At a starting pressure of 1400 psig and 74°–76° C., the dimethylphenol/acetone reactants are pumped in 77 minutes to a final pressure of 1815 psig. After a total reaction time of 273 minutes, while maintaining a pressure range of 1721–1906, 100% conversion of dimethylphenol is realized. The major isomer (VI) of a total of three isomers represented 16.05 g on 31% selectivity based on dimethylphenol. A total 36% selectivity represented all isomers.

Example 17: 2-Methyl-2(p-Methoxyphenyl) Propionic Acid (VII)

A solution of 27.1 g anisole (0.25 moles) and 43.8 g acetone (0.75 moles) is pumped into a CO pressurized reactor containing 92 g of hydrogen fluoride (4.6 moles) and 10 g water (0.56 moles). At 1516 psi total pressure and 73°–76° C., the acetone and anisole reactants are pumped over 60 minutes, and the reactor pressure is maintained at 1775–2055 psi. After a total reaction time of 295 minutes (inclusive of pumping time), 25.4 g of the methoxyphenyl acid (VII) as toluene soluble represented a 70% selectivity to VII based on anisole with a 74% conversion. Product VII is crystallized from cyclohexane yielding white crystals, nmr pure, and melting at 86°–88° C.

The following examples illustrate the use of both aqueous and anhydrous HCl activity in the alkylation/carbonylation of phenol by acetone and CO.

Example 18

In a Hastelloy C Autoclave Engineer Reactor, 80 ml concentrated hydrochloric acid charged to 21.8 g (0.23 mole) of phenol. The reactor is sealed, flushed twice with carbon monoxide, and pressurized to 1420 psig with carbon monoxide. At a reaction temperature of 120° C., 13.5 g acetone (0.23 mole) is charged into the reactor vapor space in 38 minutes. The reaction is continued at 120° C. at pressures of 1839–1900 psig for five hours. The cooled, dark brown reaction mixture is dissolved in methyl isobutyl ketone (600 ml), washed twice with water (800 ml) and extracted with 5% aqueous sodium bicarbonate solution three times (1500 ml). The combined bicarbonate solution was then acidified with 20% aqueous sulfuric acid, extracted with ether three times (600 ml), dried over $MgSO_4$ and concentrated to give a pale yellow solid product. The product was purified by washing off phenol with toluene and recrystallizing from chloroform, and identified as 2-methyl-2-(p-hydroxyphenyl) propionic acid (I) by IR, TLC and m.p. with authentic sample. The yield was 1.1 g (3.0% based on acetone charged).

Example 19

65.0 g phenol (0.69 mole) is charged to a Hastelloy C Autoclave. The reactor is sealed and pressurized with 19.4 g (550 psig) of anhydrous HCl. The reactor contents are stirred at room temperature for four minutes, pressurized to 1412 psig with carbon monoxide and heated to 120° C. Acetone (16.2 g, 0.28 mole) is then pumped to the reactor head space in 48 minutes. The reaction is allowed to proceed at 120° C. and at pressures of 1839–1995 psig for four hours. The procedure for product isolation is the same as described in Example 18. The yield of 2-methyl-2-(p-hydroxyphenyl) propionic acid is 3.6 g (7.9% based on acetone charged).

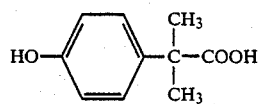

I

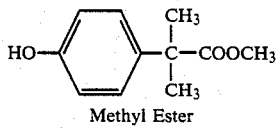

Methyl Ester

IA

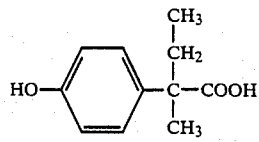

II

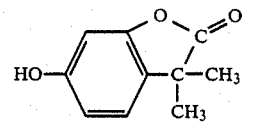

III

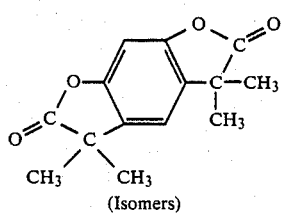

(Isomers)

IV

-continued

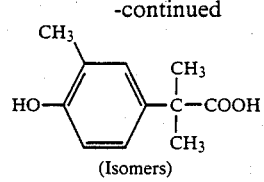

(Isomers)

V

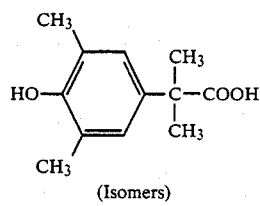

(Isomers)

VI

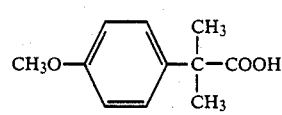

VII

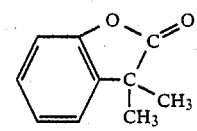

VIII

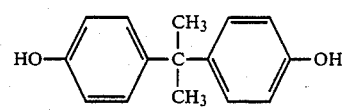

IX

The present invention provides a one step method of producing a hydroxy aryl acid or ether aryl acid as well as the methyl esters thereof. These are very useful as active compounds in various polymeric and pharmaceutical uses.

Accordingly, having described our invention as well as its advantages we claim:

1. A method of forming a carboxylic aromatic acid comprising;
   reacting an aromatic compound with a ketone and carbon monoxide in the presence of an acid, said aromatic compound having the following general formula

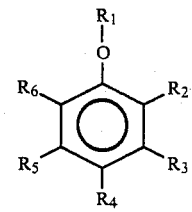

wherein $R_1$ represents a radical selected from the group consisting of H, methyl and phenyl;
wherein $R_2$–$R_6$ represent H, $C_1$–$C_{18}$ alkyl, hydroxyl, aryl, halogen, $C_1$–$C_{18}$ alkyl halide, and $C_1$–$C_{18}$ alkyl aryl and wherein at least one of $R_2$, $R_4$ and $R_6$ represent hydrogen; and
wherein said ketone comprises a $C_3$–$C_{20}$ aliphatic or aromatic ketone.

2. The method claimed in claim 1 wherein $R_1$ represents H.

3. The method claimed in claim 1 wherein $R_2$–$R_5$ represents hydrogen and $R_6$ represents $C_1$–$C_{18}$ alkyl.

4. The method claimed in claim 1 wherein $R_2$ and $R_6$ represent $C_1$–$C_{18}$ alkyl and $R_3$–$R_5$ represent H.

5. The method claimed in claim 1 wherein Ar—O—$R_1$ represents a compound selected from the group consisting of phenol, resorcinol, ortho cresol, bisphenol-A, Dimethylphneol, anisole.

6. The method claimed in claim 1 wherein said ketone is selected from the group consisting of acetone, butanone, pentanone, methyl phenyl ketone and diphenyl ketone.

7. The method claimed in claim 1 wherein said acid is selected from the group consisting of HF, HCl, $H_2SO_4$.

8. The method claimed in claim 7 wherein said acid is HF.

9. The method claimed in claim 8 wherein said acid is 80%–90% hydrofluoric acid and $H_2O$.

10. A method of forming a carboxylic aromatic acid comprising;
reacting an aromatic compound with a ketone and carbon monoxide in the presence of an acid, said aromatic compound having the following general formula

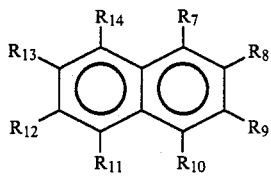

wherein at least one of said $R_7$–$R_{14}$ represents —O—$R_1$ and wherein there is at least one reactive sight within 1-3 carbon atoms from said —O—$R_1$;
wherein the remainder $R_7$–$R_{14}$ represents H, $C_1$–$C_{18}$ alkyl, halogen, hydroxyl, $C_1$–$C_{18}$ alkyl halide, $C_1$–$C_{18}$ alkyl ether, aryl alkyl; and
wherein said ketone comprises a $C_3$–$C_{20}$ aromatic or aliphatic ketone; and
wherein $R_1$ represents a group selected from H, methyl and phenyl.

11. The method claimed in claim 10 wherein said aromatic alcohol represents 1- or 2-naphthol.

12. A method of forming a methyl ester of a carboxylic aromatic acid comprising reacting an aromatic compound with a ketone and carbon monoxide and methanol in the presence of an acid; said aromatic compound having the following general formula

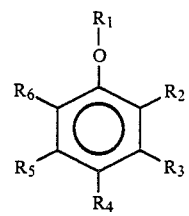

wherein $R_1$ represents a group selected from H, methyl and phenyl;
wherein $R_2$–$R_6$ represent H, $C_1$–$C_{18}$ alkyl, hydroxyl, aryl, halogen, $C_1$–$C_{18}$ alkyl halide and $C_1$–$C_{18}$ alkyl aryl; and
wherein at least $R_2$, $R_4$ and $R_6$ represent hydrogen; and
wherein said ketone is selected from the group consisting of $C_3$–$C_{20}$ aliphatic and aromatic ketones.

13. The method claimed in claim 12 wherein $R_1$ represents H.

14. The method claimed in claim 12 wherein said aromatic compound represents a compound selected from the group consisting of phenol, resorcinol, ortho cresol, bisphenol-A, Dimethylphenol, and anisole.

15. The method of forming 2-methyl-2-(p-hydroxyphenyl) propionic acid comprising reacting phenol with acetone and carbon monoxide in the presence of an acid wherein said acid is selected from a group consisting of anhydrous HF hydrofluoric acid, hydrochloric acid, and sulfuric acid.

16. A method of forming a methyl ester of a carboxylic aromatic acid comprising:
reacting an aromatic compound with a ketone and carbon monoxide and methanol in the presence of an acid,
said aromatic compound having the following general formula: Ar—O—$R_1$
wherein Ar represents an aromatic ring having a reactive site ortho or para to said —O—$R_1$; and
wherein $R_1$ represents a group selected from H, methyl and phenyl.

* * * * *